US010722862B2

(12) United States Patent
Bouvier et al.

(10) Patent No.: US 10,722,862 B2
(45) Date of Patent: Jul. 28, 2020

(54) ZEOLITIC ADSORBENTS, THEIR PROCESS OF PREPARATION AND THEIR USES (71) Applicants: CECA S.A., La Garenne Colombes (FR); IFP ENERGIES NOUVELLES, Rueil-Malmaison (FR)

(72) Inventors: Ludivine Bouvier, Orthez (FR); Stephane Kieger, Sartrouville (FR); Catherine Laroche, Vernaison (FR); Philibert Leflaive, Mions (FR)

(73) Assignees: ARKEMA FRANCE, Colombes (FR); IFP ENERGIES NOUVELLES, Rueil-Malmaison (FR)

(*) Notice: Subject to any disclaimer, the term of this patent is extended or adjusted under 35 U.S.C. 154(b) by 0 days.

(21) Appl. No.: 14/650,780

(22) PCT Filed: Dec. 10, 2013

(86) PCT No.: PCT/EP2013/076021
§ 371 (c)(1),
(2) Date: Jun. 9, 2015

(87) PCT Pub. No.: WO2014/090771
PCT Pub. Date: Jun. 19, 2014

(65) Prior Publication Data
US 2015/0306565 A1    Oct. 29, 2015

(30) Foreign Application Priority Data

Dec. 12, 2012  (FR) ..................................... 12 61964

(51) Int. Cl.
| B01J 20/18 | (2006.01) |
| B01J 20/28 | (2006.01) |
| C07C 29/76 | (2006.01) |
| C07C 37/82 | (2006.01) |
| C07C 7/13 | (2006.01) |
| B01J 20/30 | (2006.01) |

(52) U.S. Cl.
CPC ............ B01J 20/18 (2013.01); B01J 20/183 (2013.01); B01J 20/186 (2013.01); B01J 20/2803 (2013.01); B01J 20/28004 (2013.01); B01J 20/28011 (2013.01); B01J 20/3007 (2013.01); B01J 20/3042 (2013.01); B01J 20/3071 (2013.01); B01J 20/3078 (2013.01); C07C 7/13 (2013.01); C07C 29/76 (2013.01); C07C 37/82 (2013.01)

(58) Field of Classification Search
CPC .... B01J 20/18; B01J 20/2803; B01J 20/3007; B01J 20/3042; B01J 20/3071; B01J 20/3078; C07C 7/13; C07C 29/76; C07C 37/82
See application file for complete search history.

(56) References Cited

U.S. PATENT DOCUMENTS

| 2,985,589 | A | 5/1961 | Broughton |
| 3,119,660 | A | 1/1964 | Howell |
| 3,558,730 | A | 1/1971 | Neuzil |
| 3,558,732 | A | 1/1971 | Neuzil |
| 3,626,020 | A | 12/1971 | Neuzil |
| 3,663,638 | A | 5/1972 | Neuzil |
| 3,878,127 | A | 4/1975 | Rosback |
| 3,960,774 | A | 6/1976 | Rosback |
| 4,402,832 | A | 9/1983 | Gerhold |
| 4,498,991 | A | 2/1985 | Oroskar |
| 5,284,992 | A | 2/1994 | Hotier |
| 5,629,467 | A | 5/1997 | Hotier |
| 7,452,840 | B2 | 11/2008 | Plee |
| 7,812,208 | B2 | 10/2010 | Cheng |
| 7,820,869 | B2 | 10/2010 | Priegnitz |
| 8,530,367 | B2 | 9/2013 | Bouvier |
| 8,735,643 | B2 | 5/2014 | Bouvier |
| 9,050,581 | B2 | 6/2015 | Bouvier |
| 2010/0113854 | A1 | 5/2010 | Bouvier et al. |
| 2011/0124942 | A1 | 5/2011 | Bouvier et al. |
| 2011/0184165 | A1* | 7/2011 | Bouvier ........... B01J 20/18 536/127 |

FOREIGN PATENT DOCUMENTS

| FR | 2789914 | 8/2000 |
| FR | 2903978 | 1/2008 |
| FR | 2925366 | 6/2009 |
| FR | 2925367 | 6/2009 |
| WO | 2008009845 | 1/2008 |

OTHER PUBLICATIONS

ATSDR, Mar. 3, 2011, pp. 1-2.*
International Search Report for International Application No. PCT/EP2013/076021 dated Jan. 29, 2014.
Ruthven, D. et al., "Principles of adsorption and adsorption processes," 1984, pp. 326, 407, 220-323, John Wiley & Sons.
Schumann, K., et al., "Investigation on the pore structure of binderless zeolite 13x shapes," May 15, 2012, pp. 119-123, vol. 154, Microporous and Mesoporous Materials (Abstract only).

(Continued)

Primary Examiner — Colin W. Slifka
Assistant Examiner — Michael Forrest
(74) Attorney, Agent, or Firm — RatnerPrestia (57) ABSTRACT The present invention relates to zeolitic adsorbents based on small agglomerated crystals of zeolite X comprising barium, combining optimum properties in terms of selectivity and of mechanical strength.

These adsorbents have applications in the separation of fractions of aromatic $C_8$ isomers and in particular xylenes, in the separation of substituted toluene isomers, such as nitrotoluene, diethyltoluene or toluenediamine, in the separation of cresols and in the separation of polyhydric alcohols, such as sugars.

20 Claims, 1 Drawing Sheet (56) References Cited

OTHER PUBLICATIONS

Written Opinion of the International Searching Authority for International Application No. PCT/EP2013/076021 dated Jan. 29, 2014.
Breck, D.W., Zeolite Molecular Sieves, John Wiley and Sons, New York, 1973, pp. 313-315.
Xihong, L., "Primary Analysis on State of Xylene Adsorption Unit," Specialty Petrochemicals, Jun. 2004, pp. 54-55, Abstract only.
Korean Examination Report for Application No. UAE/P/619/2015, dated Nov. 4, 2019, 5 pages.

\* cited by examiner

ZEOLITIC ADSORBENTS, THEIR PROCESS OF PREPARATION AND THEIR USES

CROSS-REFERENCE TO RELATED APPLICATIONS

This application is a national phase of International Application No. PCT/EP2013/076021, filed Dec. 10, 2013, which claims priority from French Application No. 1261964, filed Dec. 12, 2012. The entire disclosures of each of these applications are incorporated herein by reference in their entirety for all purposes.

TECHNICAL FIELD

The invention relates to adsorbents, in the form of agglomerates (agglomerated zeolitic adsorbent) based on small crystals of zeolites X comprising barium or barium and potassium, to their process of preparation and to their uses.

These adsorbents exhibit both an optimized adsorption capacity and an optimized mechanical strength and can be used more particularly for the production of very pure para-xylene from a feedstock of aromatic hydrocarbons comprising isomers having 8 carbon atoms.

PRIOR ART

The use of agglomerated zeolitic adsorbents composed of zeolites X or Y comprising, in addition to sodium cations, barium, potassium or strontium ions, alone or as mixtures, in order to selectively adsorb para-xylene in a mixture of aromatic hydrocarbons, is well known from the prior art.

U.S. Pat. Nos. 3,558,730, 3,558,732, 3,626,020 and 3,663,638 show that zeolitic adsorbents comprising aluminosilicates based on sodium and barium (U.S. Pat. No. 3,960,774) or based on sodium, barium and potassium, are effective for the separation of para-xylene present in aromatic $C_8$ fractions (fractions comprising aromatic hydrocarbons having 8 carbon atoms).

The zeolitic adsorbents described in U.S. Pat. No. 3,878,127 are used as adsorption agents in liquid-phase processes, preferably of simulated countercurrent type, similar to those described in U.S. Pat. No. 2,985,589 and which apply, inter alia, to aromatic $C_8$ fractions.

In the patents listed above, the zeolitic adsorbents are provided in powder form or in the form of agglomerates composed predominantly of zeolites and up to 20% by weight of an inert binder.

The synthesis of zeolites X is usually carried out by nucleation and crystallization of aluminosilicate gels. Generally, the crystals of zeolites are prepared from aqueous sodium-comprising solutions (for example, aqueous sodium hydroxide solution), and, if desired, the sodium cations can be replaced by (exchanged with), in all or in part, other cations, for example barium or barium and potassium. These cation exchanges can be carried out before and/or after agglomeration of the pulverulent zeolite with the agglomeration binder, according to conventional techniques known to a person skilled in the art.

The synthesis of zeolites X results in crystals (generally in the powder form), the use of which on the industrial scale is particularly difficult (significant pressure drops during the handling operations). Preference is then given to the agglomerated forms of these crystals, in the form of grains, spun products and other agglomerates, it being possible for these said forms to be obtained by extrusion, pelletizing and other agglomeration techniques known to a person skilled in the art. These agglomerates do not exhibit the disadvantages inherent in pulverulent materials.

These agglomerates, whether in the form of blocks, beads, extrudates and others, are generally composed of crystals of zeolite(s), which constitute the active component (in the sense of the adsorption), and of a binder intended to ensure the cohesion of the crystals in the form of agglomerates and to confer on them a mechanical strength sufficient to withstand the vibrations and movements to which they are subjected during the operations for separation of the isomers from the aromatic $C_8$ fractions.

However, the adsorption properties of these agglomerates are obviously reduced in comparison with the powder formed of crystals, due to the presence of agglomeration binder which is inert with regard to the adsorption.

Various means have already been proposed for overcoming this disadvantage of the agglomeration binder being inert with regard to the adsorption performances, including the conversion of all or at least a portion of the agglomeration binder into zeolite active from the viewpoint of the adsorption. This operation is now well known to a person skilled in the art, for example under the name of "zeolitization". In order to easily carry out this operation, use is made of zeolitisable binders, generally belonging to the kaolinite family, and preferably calcined beforehand at temperatures generally of between 500° C. and 700° C.

An alternative form consists in moulding kaolin grains and in then zeolitizing the kaolin; the principle thereof is set out in "Zeolite Molecular Sieves" by D. W. Breck, John Wiley and Sons, New York (1973), p. 313 et seq. This technology has been successfully applied to the production of grains of zeolite A or zeolite X, up to 95% by weight composed of the zeolite itself and of a residue of unconverted binder (see, for example, U.S. Pat. No. 3,119,660, where it is found that the production of zeolite X requires the addition of a source of silica to the reaction medium).

Patent Application FR 2 789 914 describes a process for the manufacture of agglomerates based on zeolite X, with an Si/Al ratio of between 1.15 and 1.5, exchanged with barium and optionally with potassium, by agglomerating the powder of the said zeolite X with a binder, a source of silica and carboxymethylcellulose, and by then zeolitizing the binder by immersion of the agglomerate in an alkaline liquor. After exchange of the ions of the zeolite with barium ions (and optionally potassium ions) and activation, the agglomerates thus obtained exhibit, from the viewpoint of the adsorption of the para-xylene present in aromatic $C_8$ fractions, improved properties in comparison with adsorbents prepared from the same amount of zeolite X and binder but for which the binder is not zeolitized.

More recently, U.S. Pat. No. 7,820,869 describes a process for the separation of the para-xylene present in aromatic fractions by using an adsorbent of "binderless" type, that is to say devoid of amorphous material or with an amount of amorphous material of less than 2% by weight, based on zeolite X, the loss on ignition of which is between 3% and 5%. These adsorbents are obtained after a stage of zeolitization of the binder and do not comprise, or only in an amount of less than 2% by weight and often of less than 0.5% by weight, of amorphous or non-zeolitic material. They exhibit an improved adsorption capacity and improved transfer properties for low-temperature separation processes having short cycle times. On the other hand, no information is given on the mechanical strength of such "binderless" particles.

In addition to good selectivity properties with regard to the entity to be separated from the reaction mixture, the adsorbent has to exhibit good material transfer properties in order to guarantee a number of theoretical plates sufficient to carry out efficient separation of the entities in a mixture, as is shown by Ruthven in the work entitled "Principles of Adsorption and Adsorption Processes", John Wiley & Sons (1984), pages 326 and 407. Ruthven shows (ibid., page 243) that, in the case of an adsorbent in the form of agglomerates (agglomerated zeolitic adsorbent), the overall material transfer depends on the addition of the intracrystalline diffusional resistance and the diffusional resistance between the crystals. The intracrystalline diffusional resistance is proportional to the square of the radii of the crystals and inversely proportional to the diffusivity of the intracrystalline molecules.

The diffusional resistance between the crystals (also known as macropore resistance) is, for its part, proportional to the square of the radii of the agglomerates and inversely proportional to the diffusivity of the molecules in the macropores. For a given zeolite structure, a given agglomerate size and a given operating temperature, the diffusivities are fixed and the only means of improving the material transfer consists in reducing the diameter of the crystals. An increase with regard to the overall transfer will thus be obtained by reducing the size of the crystals.

In order to estimate this improvement in the transfer kinetics, use may be made of the theory of the plates described by Ruthven in "Principles of Adsorption and Adsorption Processes", ibid., pages 248-250. This approach is based on the representation of a column by a finite number of hypothetical reactors which are ideally stirred (theoretical stages). The equivalent height of theoretical plates is a direct measurement of the axial dispersion and of the resistance to material transfer of the system.

U.S. Pat. No. 7,812,208 describes a process for the separation of para-xylene present in aromatic fractions using an adsorbent of "binderless" type, that is to say without amorphous material or with an amount of amorphous material of less than 2% by weight, based on zeolite X, having a mean crystal size of less than 1.8 µm. These adsorbents are obtained after a stage of zeolitization of the binder. These adsorbents exhibit improved transfer and adsorption properties and do not comprise, or only in an amount of less than 2% by weight and often of less than 0.5% by weight, amorphous or non-zeolitic material. On the other hand, no information is given with regard to the mechanical strength of such "binderless" particles.

A third property of the adsorbent necessary in order to guarantee a good performance of the liquid-phase separation process of simulated countercurrent type is to have a good mechanical strength. This is because, under standard operating conditions for this type of process, a significant mechanical stress is applied to the adsorbent within the industrial units, resulting in the formation of fine particles, which bring about a deterioration in the performance (see, for example, "Primary Analysis on State of Xylene Adsorption Unit", Li et al., Jingxi Shiyou Huagong, 2004 (4), 54-55), this increasing in proportion as the mechanical strength of the adsorbent decreases.

Thus, Patent Application FR 2 903 978 describes a process for the manufacture of agglomerates based on zeolite X, having small crystals, with a size of less than 1.7 µm, with an Si/Al molar ratio such that $1.15 < Si/Al \leq 1.5$, exchanged with barium and optionally with potassium, by agglomerating zeolite X powder with a binder, a source of silica, and by then zeolitizing the binder by immersion of the agglomerates in an alkaline liquor. After exchange of the ions of the zeolite with barium ions (and optionally potassium ions) and activation, the agglomerates thus obtained exhibit improved transfer properties in processes for the separation of para-xylene present in aromatic fractions while reinforcing their mechanical strength.

Consequently, it is known that agglomerated zeolitic adsorbents based on zeolite X exchanged with barium (or barium and potassium) exhibit good properties of adsorption of xylenes and a good selectivity for the para-xylene present in aromatic $C_8$ fractions, in the liquid phase.

Furthermore, it is known from WO 2008/009845 that small crystals of zeolite(s) generally contribute a better material transfer but a poorer mechanical strength than the crystals of the same zeolite of greater size.

A person skilled in the art thus expects agglomerated zeolitic adsorbents, based on zeolite X, having small crystals, comprising barium (or barium and potassium), to exhibit good properties of adsorption of para-xylene, a good selectivity and a good material transfer and thus expects such adsorbents to exhibit good initial performances of separation of the para-xylene present in aromatic $C_8$ fractions in a liquid-phase process, for example of simulated countercurrent type.

The prior art teaches that the zeolitization of agglomerated adsorbents makes it possible to increase the adsorption capacity. From the prior art, a person skilled in the art understands that he can carry out a complete conversion of the binder to zeolite in order to obtain a maximum adsorption capacity without a priori affecting the mechanical properties of the said agglomerated adsorbents.

In point of fact, the inventors have now discovered that, after complete conversion of the binder to zeolite, the mechanical properties are not always retained or optimized. A need consequently remains for agglomerated zeolitic adsorbents exhibiting good mechanical properties and good selectivity properties, in particular from the viewpoint of the separation of xylene isomers from aromatic $C_8$ fractions. The inventors have thus discovered that there exists a compromise between adsorption optimum and mechanical strength optimum.

It is thus an objective of the present invention to provide agglomerated zeolitic adsorbents, based on zeolite X, having small crystals, comprising barium or barium and potassium, the said adsorbents combining:

a good selectivity,
an improved material transfer,
an optimum adsorption capacity and
a good mechanical strength, for the separation of the para-xylene present in aromatic $C_8$ fractions in a liquid-phase process, for example of simulated countercurrent type.

The inventors have found that the zeolitic adsorbents, based on zeolite X, having small crystals, agglomerated with a zeolitisable binder, the binder of which has been subjected to a complete or virtually complete zeolitization reaction, so as to respectively completely or virtually completely convert the binder into active material, do not exhibit a maximum adsorption capacity or a good mechanical strength.

The inventors have discovered that the best compromise between maximum adsorption capacity and high mechanical strength takes place not for a maximum degree of zeolitization but for a degree of zeolitization such that the content of non-zeolitic phase of the adsorbent is between 2% and 5% by weight, with respect to the total weight of the said adsorbent.

ACCOUNT OF THE INVENTION

A first subject-matter of the present invention is thus an agglomerated zeolitic adsorbent, having optimized properties, in particular for the separation of para-xylene from aromatic $C_8$ fractions. The agglomerated zeolitic adsorbent exhibits maximum properties of selectivity with regard to para-xylene and of material transfer, while exhibiting a maximum mechanical strength in combination with an optimized adsorption capacity, and is particularly suitable for use in a process for the separation of para-xylene in the liquid phase, preferably of simulated countercurrent type.

Thus, the present invention relates to an agglomerated zeolitic adsorbent, based on crystals of zeolite X and on at least one non-zeolitic phase, in which adsorbent:
the crystals of zeolite X exhibit:
  i. a number-average diameter of less than or equal to 1.7 μm, preferably of less than or equal to 1.5 μm and more preferably of less than or equal to 1.2 μm,
  ii. an Si/Al atomic ratio of between 1.00 and 1.50, preferably between 1.05 and 1.50 and more preferably between 1.10 and 1.50, limits included,
the content by weight of non-zeolitic phase (NZP) is such that 2.0%<NZP<5.0%, preferably such that 3.0%<NZP<5.0%, more preferably such that 3.0%<NZP<4.0%, advantageously such that 3.2%<NZP<3.7%, by weight of the total weight of the adsorbent,
the content by weight of barium oxide (BaO) is greater than 23%, preferably greater than 32% and more preferably greater than 33%, with respect to the total weight of the adsorbent,
the content by weight of potassium oxide $K_2O$ is less than 9%, preferably less than 8% and more preferably between 0% and 2%, advantageously between 0% and 1%, limits included, with respect to the total weight of the adsorbent, and
the total content by weight of oxides of alkali metal or alkaline earth metal ions, other than BaO and $K_2O$, is less than 5% and is preferably between 0% and 2% and advantageously between 0% and 1%, limits included, with respect to the total weight of the adsorbent.

The agglomerated zeolitic adsorbent according to the present invention is an adsorbent based on crystals of zeolite of faujasite type, generally referenced under the name of type X. The term "zeolite X" is understood to mean the zeolites for which the Si/Al atomic ratio is between 1.00 and 1.50, limits included, preferably between 1.05 and 1.50, limits included, and more preferably still, between 1.10 and 1.50, limits included.

Among zeolites X, it is now commonly accepted to recognize two subgroups denoted zeolites LSX and zeolites MSX. The zeolites LSX exhibit an Si/Al atomic ratio equal to approximately 1 and the zeolites MSX exhibit an Si/Al atomic ratio of between approximately 1.05 and approximately 1.15, limits included.

According to a preferred embodiment of the present invention, the crystals of zeolite X exhibit an Si/Al atomic ratio of between 1.10 and 1.50, limits included. According to another preferred embodiment, the crystals of zeolite X are crystals of zeolite LSX with an Si/Al atomic ratio equal to approximately 1. However, the invention does not exclude the adsorbent from comprising mixtures of two or several types of zeolites X as just defined.

According to yet another preferred embodiment of the present invention, the number-average diameter of the crystals of zeolites X is advantageously between 0.1 μm and 1.5 μm, more advantageously between 0.1 μm and 1.2 μm, limits included.

The zeolitic adsorbents according to the present invention thus comprise crystals of zeolite(s) X and at least one non-zeolitic phase (NZP), that is to say a noncrystalline phase which is essentially inert with regard to the adsorption. The degree of crystallinity of the adsorbent according to the invention is measured by X-ray diffraction analysis, known to a person skilled in the art under the acronym XRD.

The zeolitic adsorbent of the invention is preferably in the form of agglomerates, that is to say that it is composed of crystals of zeolite(s) and of at least one non-zeolitic phase comprising at least one agglomeration binder which makes possible the cohesion of the crystals with one another. The agglomerated zeolitic adsorbent of the invention is denoted without distinction agglomerated zeolitic adsorbent, zeolitic adsorbent or more simply still agglomerate(s) in the continuation of the present account.

According to yet another embodiment of the invention, the zeolitic adsorbent exhibits a content by weight of barium oxide (BaO) of between 33% and 42%, limits included, and typically between 35% and 38%, limits included, with respect to the total weight of the adsorbent.

According to a preferred embodiment, the zeolitic adsorbent according to the invention exhibits a loss on ignition, measured at 950° C. according to Standard NF EN 196-2, of between 4.0% and 7.7%, preferably between 4.5% and 6.5% and advantageously between 4.8% and 6%, limits included.

As indicated above, the zeolitic adsorbent according to the present invention surprisingly exhibits an optimum compromise between adsorption capacity and mechanical strength. This mechanical strength is measured by the Shell Method Series SMS1471-74 adapted for agglomerates with a size of less than 1.6 mm and is generally greater than or equal to 1.8 MPa, more generally greater than or equal to 2 MPa, and typically greater than or equal to 2.1 MPa.

For its part, the adsorption capacity is quantified by measurement of the micropore volume of the adsorbent, which volume is evaluated by the Dubinin-Raduskevitch equation by nitrogen ($N_2$) adsorption at a temperature 77K, after degassing under vacuum at 300° C. for 16 hours. The micropore volume of the zeolitic adsorbents of the invention was thus measured as being greater than 0.250 $cm^3/g$, typically within a range extending from 0.256 $cm^3/g$ to 0.288 $cm^3/g$.

According to another aspect, the invention relates to a process for the preparation of the agglomerated zeolitic adsorbents as just defined, which process comprises at least the stages of:
  a) agglomeration of crystals of zeolite X with a number-average diameter of less than or equal to 1.7 μm, preferably of less than or equal to 1.5 μm and more preferably of less than or equal to 1.2 μm, with an Si/Al atomic ratio of between 1.00 and 1.50, preferably between 1.05 and 1.50 and more preferably still of between 1.10 and 1.50, limits included, with a binder comprising at least 80% by weight, preferably at least 90% by weight, and more preferably at least 95% by weight of zeolitisable clay and with a source of silica, then shaping of agglomerates and, finally, drying and calcination of said agglomerates,
  b) zeolitization of the said zeolitisable binder by bringing the agglomerates obtained in stage a) into contact with a basic alkaline solution, c) cationic exchange of the agglomerates of stage b) by bringing into contact with a solution of barium ions or of barium ions and potassium ions, d) optional cationic exchange by bringing the agglomerates of stage c) into contact with a solution of potassium ions, e) then washing and drying the agglomerates thus obtained, and f) production of the zeolitic adsorbent by activation of the agglomerates obtained in stage e).

The size of the crystals of zeolite X used in stage a) and of the crystals of zeolite X in the agglomerates is measured by observation using a scanning electron microscope (SEM). This SEM observation also makes it possible to confirm the presence of non-zeolitic phase comprising, for example, residual binder (binder not converted during the zeolitization stage) or any other amorphous phase in the agglomerates.

The commonest commercial crystals of zeolite X generally exhibit a diameter of greater than or equal to 1.8 µm. The crystals employed in the context of the present invention preferably exhibit a number-average diameter of less than or equal to 1.7 µm, preferably strictly of less than 1.5 µm and better still of less than or equal to 1.2 µm. The crystals for which the number-average diameter is strictly less than 1.2 µm are regarded as very small crystals. In the present document, the term "number-average diameter" or else "size" is employed for the zeolite crystals and for the agglomerates. The method for measuring these quantities is explained later in the description.

The agglomeration and the shaping (stage a) can be carried out according to any technique known to a person skilled in the art, such as extrusion, compacting, agglomeration and others. The proportions of agglomeration binder (see definition later) and of zeolite employed are typically those of the prior art, that is to say from 5 parts to 20 parts by weight of binder per 95 parts to 80 parts by weight of zeolite. The agglomerates resulting from stage a), whether in the form of beads, extrudates or others, generally have a number-average diameter, or their length (greater dimension when they are not spherical), of between 0.4 mm and 2 mm, in particular of between 0.4 mm and 0.8 mm and preferably of between 0.4 mm and 0.65 mm, limits included.

On conclusion of stage a), the finest particles of agglomerates can be removed by cycloning and/or sieving and/or the excessively large particles can be removed by sieving or crushing, in the case of extrudates, for example.

The agglomeration binder employed in stage a) comprises at least 80% by weight, preferably at least 90% by weight, more preferably at least 95% by weight and more particularly at least 96% by weight of zeolitisable clay and can also comprise other inorganic binders, such as bentonite, attapulgite and others. The term "zeolitisable clay" is understood to mean a clay or a mixture of clays which is capable of being converted into zeolitic material, generally by action of a basic alkaline solution. The zeolitisable clay generally belongs to the family of kaolins, kaolinites, nacrites, dickites, halloysite and/or metakaolins. Kaolin is preferred and is most commonly used.

The powder formed of zeolite X employed in stage a) can result from the synthesis of crystals of zeolite X comprising predominantly, indeed even exclusively, sodium cations, for example zeolites NaX (or 13X), but it would not be departing from the scope of the invention to use a powder which has been subjected, between the synthesis in the NaX form and its use in stage a), to one or more cationic exchanges. In this case, the cationic exchange stages c) and d) consequently become unnecessary.

The optional source of silica can be of any type known to a person skilled in the art who is a specialist in the synthesis of zeolites, for example colloidal silica, diatoms, perlite, fly ash, sand or any other form of solid silica.

During stage a), in addition to the powder formed of zeolite X and the binder, additives can also be added, for example additives intended to facilitate the agglomeration or to improve the hardening of the agglomerates formed, such as lignin, starch, carboxymethylcellulose and other additives known to a person skilled in the art.

After the drying in stage a), the calcination is carried out at a temperature generally of between 500° C. and 600° C. and makes it possible to convert the zeolitisable clay, typically kaolin, into metakaolin, which can next be converted into zeolite during the zeolitization stage (stage b)). The principle thereof is set out in "Zeolite Molecular Sieves" by D. W. Breck, John Wiley and Sons, New York (1973), pp. 314-315.

The zeolitization of the agglomeration binder is carried out according to any method now well known to a person skilled in the art and can, for example, be carried out by immersion of the product from stage a) in a basic alkaline solution, generally an aqueous solution, for example, an aqueous sodium hydroxide and/or potassium hydroxide solution.

The inventors have discovered that the minimum amount by weight of non-zeolitic phase does not coincide exactly with the optimum mechanical properties of bed strength (BS), typically a BS of greater than or equal to 1.8 MPa, preferably of greater than or equal to 2 MPa, for the type of zeolitic adsorbent defined above. Consequently, the zeolitization has to be finely controlled so as to obtain the optimum compromise between amount by weight of non-zeolitic phase (NZP) and mechanical strength, in particular BS. As indicated above, the agglomerated zeolitic adsorbent of the present invention exhibits an amount by weight of non-zeolitic phase (NZP) such that 2.0%<NZP<5.0%.

The parameters which can have an influence on the optimum degree of zeolitization to be applied during the synthesis of the zeolitic adsorbent according to the invention are in particular the concentration of the alkaline solution used, the temperature at which the zeolitization is carried out and the duration of the zeolitization reaction, that is to say the residence time of the zeolitic adsorbent in the said alkaline solution used.

Thus, the zeolitization stage according to the process of the invention makes it possible to achieve a zeolitic adsorbent achieving the optimum compromise between adsorption capacity and mechanical strength, in particular BS. The examples presented later by way of illustration of the present invention show that this optimum compromise is obtained by adjusting the concentration of basic alkaline solution, the zeolitization temperature and the zeolitization duration.

As a general rule, the concentration of the alkaline zeolitization solution is preferably between 0.5M and 5M. The zeolitization is preferably carried out under hot conditions, at a temperature greater than ambient temperature, and typically at temperatures of the order of 80° C. to 100° C., for example of between ambient temperature (i.e., approximately 20° C.) and the boiling point of the alkaline zeolitization solution. The duration of the zeolitization process is generally between a few tens of minutes and a few hours, preferably between approximately 1 hour and 8 hours, more preferably between approximately 2 hours and 6 hours.

Stage c) of exchange with barium of the cations of the zeolite is carried out according to conventional methods known to a person skilled in the art and generally by bringing the agglomerates resulting from stage b) (or stage d) into contact with a barium salt, such as barium chloride ($BaCl_2$), in aqueous solution at a temperature of between ambient temperature and 100° C. and preferably of between 80° C. and 100° C. In order to rapidly obtain high contents of barium oxide, i.e. preferably greater than 32% by weight, with respect to the total weight of the agglomerate, and preferably ranging from 33% to 42% by weight and advantageously ranging from 35% to 38% by weight, with respect to the total weight of the agglomerate, it is preferable to operate with a large excess of barium ions, with respect to the cations of the zeolite which it is desired to exchange, typically an excess of the order of 10 to 12, advantageously by carrying out successive exchanges.

The optional exchange with potassium (stage d) can be carried out before and/or after the exchange with barium (stage c). As indicated above, it is also possible to agglomerate, in stage a), powder formed of zeolite X already comprising potassium ions (pre-exchange of the cations present in the starting zeolite X, typically sodium cations, with potassium ions before stage a) and to dispense (or not) with stage d).

A washing operation, generally and preferably with water, is subsequently carried out, followed by a drying operation on the agglomerate thus obtained.

The activation which follows the drying operation is carried out conventionally according to methods known to a person skilled in the art, for example at a temperature generally of between 100° C. and 400° C., preferably between 200° C. and 300° C. This stage e) of activation has the aim of fixing the water content and also the loss on ignition of the adsorbent in a way which is optimal for the use envisaged. The activation is generally carried out by thermal activation, which is preferably implemented between 200° C. and 300° C., for a period of time determined as a function of the water content desired and of the loss on ignition desired, typically from 1 to 6 hours.

The present invention also relates to the uses of the zeolitic adsorbents described above as adsorption agents capable of advantageously replacing the adsorption agents described in the literature, based on zeolite X comprising barium oxide or based on zeolite X comprising barium oxide and potassium oxide, and in particular in the uses listed below:
separation of fractions of aromatic $C_8$ isomers and in particular xylenes,
separation of substituted toluene isomers, such as nitrotoluene, diethyltoluene, toluenediamine and others,
separation of cresols,
separation of polyhydric alcohols, such as sugars.

The invention relates in particular to an improvement to the process for the recovery of para-xylene from fractions of aromatic isomers having 8 carbon atoms which consists in using, as agent for adsorption of the para-xylene, an agglomerated zeolitic adsorbent according to the invention, employed in liquid-phase processes but also in gas-phase processes, the said process preferably being carried out in the presence of a desorbent.

The desired product (para-xylene) can thus be separated by (batch) preparative adsorption liquid chromatography and advantageously continuously in a simulated moving bed, that is to say under simulated countercurrent conditions or under simulated cocurrent conditions, more particularly under simulated countercurrent conditions.

The operating conditions of an industrial adsorption unit of simulated countercurrent type are generally as follows:
number of beds 6 to 30,
number of zones: at least 4 operating zones, each being located between a feed point and a withdrawal point,
temperature of between 100° C. and 250° C., preferably between 150° C. and 190° C.,
pressure of the industrial unit between the bubble pressure of the xylenes at the temperature of the process and 3 MPa,
ratio of the desorbent to feedstock flow rates of between 0.7 and 2.5, for example between 0.9 and 1.8 for an adsorption unit alone (stand alone) and between 0.7 and 1.4 for an adsorption unit in combination with a crystallization unit,
degree of recycling of between 2.5 and 12, preferably between 3.5 and 6.

Reference may be made, with regard to this subject, to the teaching of U.S. Pat. Nos. 2,985,589, 5,284,992 and 5,629,467.

The operating conditions of a simulated cocurrent industrial adsorption unit are generally the same as those operating under simulated countercurrent conditions, with the exception of the degree of recycling, which is generally between 0.8 and 7. Reference may be made, with regard to this aspect, to U.S. Pat. Nos. 4,402,832 and 4,498,991.

The desorption solvent can be any desorbent known to a person skilled in the art with a boiling point lower than that of the feedstock, such as toluene, but also a desorbent with a boiling point greater than that of the feedstock, such as para-diethylbenzene (PDEB). The selectivity of the adsorbents according to the invention for the adsorption of the para-xylene present in aromatic $C_8$ fractions is optimum when their loss on ignition, measured at 900° C., is generally between 4.0% and 7.7% and preferably between 4.7% and 6.7%.

DESCRIPTION OF THE FIGURES

The change in the bed mechanical strength (BS) and in the content of non-zeolite phase (NZP), as a function of one of the factors which make it possible to control the zeolitization, which is in this instance the duration of the zeolitization reaction, is presented in FIG. 1. Unexpectedly, this FIGURE shows that prolonging the zeolitization time, with the aim of reducing the content of non-zeolitic phase, results on the contrary in a drastic decrease in the crystalline phase and at the same time in the bed mechanical strength of the zeolitic adsorbent. The zeolitization reaction thus has to be finely controlled in order to obtain a zeolitic adsorbent exhibiting both a capacity which is optimum in terms of adsorption and mechanical properties which are optimum in terms of bed mechanical strength.

Characterization Techniques

Particle Size Determination on the Crystals:

The number-average diameter of the crystals of zeolite X used in stage a) and of the crystals of zeolite X present in the agglomerates is estimated by observation using a scanning electron microscope (SEM).

In order to estimate the size of the zeolite crystals on the samples, a group of photographs is taken at a magnification of at least 5000. The diameter of at least 200 crystals is subsequently measured using dedicated software, for example the Smile View software from the editor LoGraMi. The accuracy is of the order of 3%.

Chemical Analysis of the Zeolitic Adsorbents—Si/Al Ratio and Degree of Exchange:

An elemental chemical analysis of the final product obtained on conclusion of stages a) to f) described above can be carried out according to different analytical techniques known to a person skilled in the art. Mention may be made, among these techniques, of the technique of chemical analysis by X-ray fluorescence, such as described in Standard NF EN ISO 12677: 2011, on a wavelength dispersive spectrometer (WDXRF), for example Tiger S8 from Bruker.

X-ray fluorescence is a nondestructive spectral technique which makes use of the photoluminescence of the atoms in the X-ray region to establish the elemental composition of the sample. The excitation of the atoms, generally by a beam of X rays or by bombardment with electrons, generates specific radiation after return to the ground state of the atom. The X-ray fluorescence spectrum has the advantage of not depending very much on the chemical combination of the element, which provides a precise determination, both quantitatively and qualitatively. There is obtained, conventionally, after calibrating, for each oxide, an uncertainty of measurement of less than 0.4% by weight.

These elemental chemical analyses make it possible both to confirm the Si/Al atomic ratio of the zeolite within the agglomerate and to confirm the quality of the ionic exchange described in stage c) and in optional stage d). In the description of the present invention, the uncertainty of measurement of the Si/Al atomic ratio is ±5%.

The quality of the ionic exchange is related to the number of moles of sodium oxide, $Na_2O$, remaining in the agglomerated zeolitic adsorbent after exchange. More specifically, the degree of exchange with barium ions is estimated by evaluating the ratio of the number of moles of barium oxide, BaO, to the number of moles of the combination BaO+$Na_2O$. Likewise, the degree of exchange with barium and potassium ions is estimated by evaluating the ratio of the number of moles of the combination barium oxide+potassium oxide (BaO+$K_2O$) to the number of moles of the combination BaO+$K_2O$+$Na_2O$. It should be noted that the contents of different oxides are given as percentage by weight, with respect to the total weight of the anhydrous zeolitic adsorbent.

Particle Size Determination on the Zeolitic Adsorbents:

The number-average diameter of the zeolitic adsorbents obtained on conclusion of stage a) of agglomeration and of shaping is determined by analysis of the particle size distribution of a sample of agglomerate by imaging according to Standard ISO 13322-2:2006, using a conveyor belt which makes it possible for the sample to pass in front of the lens of the camera.

The number-average diameter is subsequently calculated from the particle size distribution by applying Standard ISO 9276-2:2001. In the present document, the term "number-average diameter" or else "size" is employed for the agglomerated zeolitic adsorbents. The accuracy is of the order of 0.01 mm for the size range of the agglomerates of the invention.

Mechanical Strength of the Zeolitic Adsorbents:

The crushing strength of a bed of zeolitic adsorbents as described in the present invention is characterized according to the Shell Method Series SMS1471-74 (Shell Method Series SMS1471-74 "Determination of Bulk Crushing Strength of Catalysts. Compression-Sieve Method), in combination with the "BCS Tester" device sold by Vinci Technologies. This method, initially intended for the characterization of catalysts of 3 mm to 6 mm, is based on the use of a 425 µm sieve which will make it possible in particular to separate the fines created during the crushing. The use of a 425 µm sieve remains appropriate for particles with a diameter of greater than 1.6 mm but has to be adjusted according to the particle size determination on the agglomerates which it is desired to characterize.

The agglomerates of the present invention, generally in the form of beads or extrudates, generally have a number-average diameter or a length, i.e. greater dimension in the case of the nonspherical agglomerates, of between 0.4 mm and 2 mm, in particular between 0.4 mm and 0.8 mm and preferably between 0.4 mm and 0.65 mm. Consequently, a 200 µm sieve is used in place of the 425 µm sieve mentioned in the standard Shell Method SMS1471-74.

The measurement protocol is as follows: a sample of 20 $cm^3$ agglomerates, sieved beforehand with the appropriate sieve (200 µm) and dried beforehand in an oven at 250° C. (instead of 300° C. mentioned in the Standard Shell Method SMS1471-74) for at least 2 hours, is placed in a metal cylinder of known internal section. An increasing force is imposed in stepwise fashion on this sample via a piston, through a bed of 5 $cm^3$ of steel beads in order to achieve a better distribution of the force exerted by the piston on the agglomerates (use of beads with a diameter of 2 mm for particles of spherical shape having a diameter strictly of less than 1.6 mm). The fines obtained at the various pressure steps are separated by sieving (suitable sieve of 200 µm) and weighed.

The bed crushing strength is determined by the pressure in megaPascals (MPa) for which the amount of cumulative fines passing through the sieve amounts to 0.5% by weight of the sample. This value is obtained by plotting, on a graph, the weight of fines obtained as a function of the force applied to the bed of zeolitic adsorbent and by interpolating to 0.5% by weight of cumulative fines. The bed crushing mechanical strength is typically between a few hundred kPa and a few tens of MPa and generally between 0.3 MPa and 3.2 MPa. The accuracy is conventionally less than 0.1 MPa.

Non-Zeolitic Phase of the Zeolitic Adsorbents:

The content of non-zeolitic phase, for example residual non-zeolitized binder or any other amorphous phase, after zeolitization is calculated according to the following equation:

$$NZP=100-\Sigma(ZP),$$

where ZP represents the sum of the amounts of the fractions of zeolites X within the meaning of the invention.

The amount of the fractions of zeolites X is measured by X-ray diffraction analysis, known to a person skilled in the art under the acronym XRD. This analysis is carried out on a device having the Bruker trade mark and then the amount of the fractions of zeolites X is evaluated by means of the TOPAS software from Bruker.

Micropore Volume:

The crystallinity of the agglomerates is also evaluated by measuring their micropore volume, the latter being compared with that of the appropriate reference (zeolite which is 100% crystalline under conditions of cationic treatment which are identical or theoretical zeolite). This micropore volume is determined from the measurement of the gas, such as nitrogen, adsorption isotherm at its liquefaction temperature. Prior to the adsorption, the zeolitic adsorbent is degassed under vacuum (P<$6.7\times10^{-4}$ Pa) at between 300° C. and 450° C. for a period of time of 9 hours to 16 hours. The nitrogen adsorption isotherm at 77K is subsequently measured on a device of ASAP 2010 M type from Micromeritics, at least 35 measurement points being taken at relative pressures with a ratio $P/P_0$ of between 0.002 and 1. The micropore volume is determined according to Dubinin and Raduskevitch from the isotherm obtained, Standard ISO 15901-3:2007 being applied. The micropore volume evaluated according to Dubinin and Raduskevitch is expressed in $cm^3$ of liquid adsorbate per gram of adsorbent. The uncertainty in measurement is ±0.003 $g/cm^3$.

Loss on Ignition of the Zeolitic Adsorbents:

The loss on ignition is determined in an oxidizing atmosphere, by calcination of the sample in air at a temperature of 950° C.±25° C., as described in Standard NF EN 196-2 (April 2006). The measurement standard deviation is less than 0.1%.

Characterization of the Liquid-Phase Adsorption by Breakthrough:

The technique used to characterize the adsorption of molecules in the liquid phase on a porous solid is the "breakthrough" technique described by Ruthven in "Principles of Adsorption and Adsorption Processes" (Chapters 8 and 9, John Wiley & Sons, 1984), which defines the technique of breakthrough curves as the study of the response to the injection of a class of adsorbable constituents. The analysis of the mean exit time (first moment) of the breakthrough curves provides information on the amounts adsorbed and also makes it possible to evaluate the selectivities, that is to say the separation factor, between two adsorbable constituents. The injection of a nonadsorbable constituent used as tracer is recommended for the estimation of the nonselective volumes. The analysis of the dispersion (second moment) of the breakthrough curves makes it possible to evaluate the equivalent height of the theoretical plates, which is based on the representation of a column by a finite number of hypothetical reactors which are ideally stirred (theoretical stages), which is a direct measurement of the axial dispersion and of the resistance to the material transfer of the system.

EXAMPLES

Example A

Synthesis of Crystals of Zeolite X, with an Si/Al Atomic Ratio of 1.25, with a Number-Average Diameter of 1.0 μm and with an Na/Al Atomic Ratio of 1

A gel having the molar composition 3.5 $Na_2O$, 2.8 $SiO_2$, $Al_2O_3$ and 130 $H_2O$ is prepared by mixing the following reactants: sodium silicate, sodium aluminate and water. The gel is matured at 35° C. for 20 hours and a crystallization is carried out at 100° C. for 4 hours.

The crystals obtained after filtration and washing are identified by X-ray diffraction (XRD analysis) as being faujasite crystals. The chemical analysis of the solid gives an Si/Al atomic ratio of 1.25. The micropore volume, evaluated from the Dubinin-Raduskevitch equation as described in the technical characterization part and expressed in $cm^3$ per gram of dry adsorbent, is 0.345±0.003 $cm^3/g$. The size of the zeolite crystals is analysed by scanning electron microscopy and shows that their number-average diameter is 1.0 μm.

Example B

Synthesis of Crystals of Zeolite X, Si/Al=1.20, Diameter 0.8 μm

A gel having the molar composition 4 $Na_2O$, 2.8 $SiO_2$. $Al_2O_3$ and 130 $H_2O$ is prepared by mixing the reactants: sodium silicate, sodium aluminate and water, using a turbine mixer. The gel is allowed to mature at 35° C. for 20 hours and a crystallization is carried out at 100° C. for 4 hours.

The crystals obtained after filtration and washing are identified by X-ray diffraction (XRD analysis) as being faujasite crystals. The chemical analysis of the solid gives an Si/Al atomic ratio of 1.20±0.03. The micropore volume, evaluated from the Dubinin-Raduskevitch equation as described above and expressed in $cm^3/g$ of dry adsorbent, is 0.344±0.003 $cm^3/g$. The size of the zeolite crystals is analysed by scanning electron microscopy: their number-average diameter is 0.8 μm.

Preparation of the Zeolitic Adsorbents

A homogeneous mixture is prepared and 800 g of crystals of zeolite NaX, prepared according to the procedures described in Example A or Example B, are agglomerated with 105 g of kaolin (expressed as calcined equivalent) and 45 g of colloidal silica, sold under the trade name Klebosol®30 (comprising 30% by weight of $SiO_2$ and 0.5% of $Na_2O$), with the amount of water which makes possible the extrusion of the mixture. The extrudates are dried, crushed, so as to recover grains for which the number-average diameter is equal to 0.7 mm, and then calcined at 550° C. under a stream of nitrogen for 2 hours.

Example 1

200 g of agglomerates obtained from the powder synthesized in Example A are placed in a glass reactor provided with a jacket regulated at a temperature of 100° C.±1° C., 1.5 l of a 2.5M aqueous sodium hydroxide solution are then added and the reaction medium is left stirring for a period of time which can vary from 1 hour to 8 hours, as shown in the table below.

The agglomerates are subsequently washed in 3 successive operations of washing with water, followed by the emptying of the reactor. It is ascertained that the washing is effective by measuring the final pH of the aqueous wash liquors of between 10.0 and 10.5.

These agglomerates are used in a cationic exchange reaction by action of a 0.5M aqueous barium chloride solution at 95° C. in 4 stages. At each stage, the ratio of volume of solution to weight of solid is 20 ml/g and the exchange is continued for 4 hours on each occasion. Between each exchange, the solid is washed several times, so as to free it from excesses of salt. The agglomerates are subsequently dried at 80° C. for 2 hours and finally activated at 250° C. for 2 hours under a stream of nitrogen.

The various products are characterized in order to determine, by all the analytical techniques described above: the content of non-zeolitic phase (NZP), the micropore volume according to Dubinin-Raduskevitch (DR Vol) and the bed mechanical strength (BS). The results are given in Table 1.

The loss on ignition, measured as described above, is 5.4%±0.1% for each sample. The degree of barium exchange of the agglomerates, calculated from the elemental analyses of the barium oxide and sodium oxide by WDXRF as described in the characterization techniques, is 99.7±0.2%.

TABLE 1

| Duration (h) | BS (MPa) | DR Vol ($cm^3/g$) | NZP |
|---|---|---|---|
| 1 | 1.67 | 0.250 | 6.4% |
| 2 | 1.83 | 0.254 | 4.9% |
| 3 | 2.17 | 0.257 | 3.7% |

TABLE 1-continued

| Duration (h) | BS (MPa) | DR Vol (cm³/g) | NZP |
|---|---|---|---|
| 4 | 2.62 | 0.258 | 3.4% |
| 5 | 2.00 | 0.261 | 2.2% |
| 6 | 1.80 | 0.256 | 4.0% |
| 7 | 1.25 | 0.249 | 6.7% |
| 8 | 0.93 | 0.236 | 11.6% |

Figure 1:
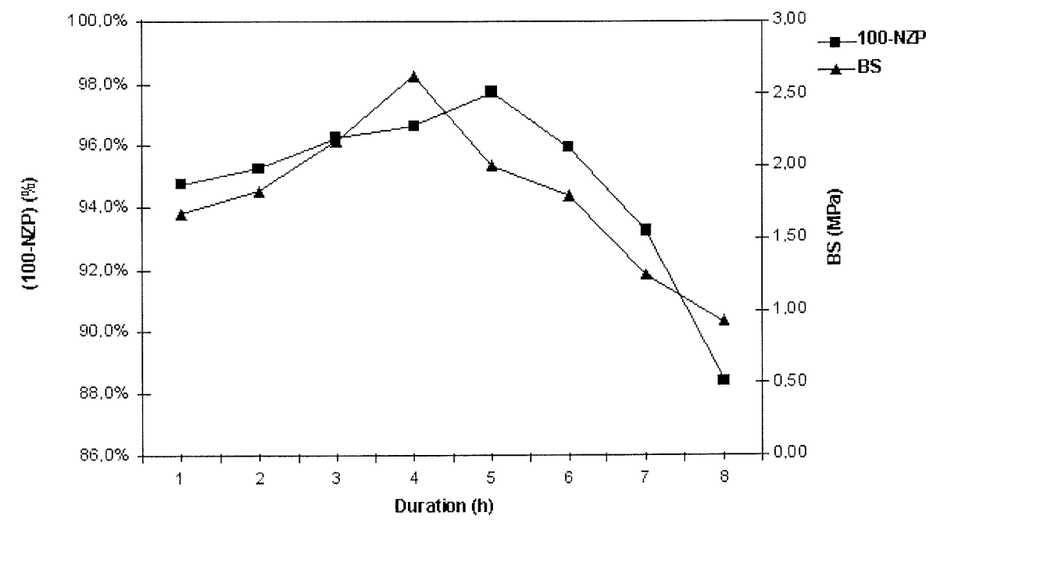

The values of Table 1 are given in graphical form in FIG. 1. It is found that it is impossible to obtain agglomerated zeolitic adsorbents which combine both a maximum adsorption capacity and a maximum mechanical strength. An optimum adsorption capacity/optimum mechanical strength compromise is then obtained for a content of non-zeolitic phase (NZP) of between 2% and 5% by weight, with respect to the weight of the agglomerate, and measured by XRD.

Example 2

Tests with Different Concentrations of Sodium Hydroxide 200 g of agglomerates obtained from the powder synthesized in Example A are placed in a glass reactor provided with a jacket regulated at a temperature of 100° C.±1° C., 1.5 l of an aqueous sodium hydroxide solution having a concentration ranging from 0.5M to 5.5M, as shown in Table 2, are then added and the reaction medium is left stirring for a duration of 4 to 5 hours.

The agglomerates are subsequently washed in 3 successive operations of washing with water, followed by the emptying of the reactor. It is ascertained that the washing is effective by measuring the final pH of the aqueous wash liquors, which is between 10.0 and 10.5.

These agglomerates are exchanged, as described in Example 1, by means of a 0.5M barium chloride solution at 95° C. in 4 stages. At each stage, the ratio of volume of solution to weight of solid is 20 ml/g and the exchange is continued for 4 hours on each occasion. Between each exchange, the solid is washed several times so as to free it from the excesses of salt. The agglomerates are subsequently dried at 80° C. for 2 hours and finally activated at 250° C. for 2 hours under a stream of nitrogen.

The various products are characterized in order to determine, by all the analytical techniques described above: the loss on ignition, the content of non-zeolitic phase, the micropore volume and the mechanical strength. The results are given in Table 2 below.

The degree of barium exchange of the agglomerates, calculated from the elemental analyses of the barium oxide and sodium oxide by WDXRF as described in the characterization techniques, is 99.6±0.2%. The loss on ignition, measured as described above, is 5.3%±0.1% for each sample.

TABLE 2

| Concentration (M) | BS (MPa) | DR Vol (cm³/g) | NZP |
|---|---|---|---|
| 0.5 | 1.20 | 0.242 | 9.7% |
| 2.5 | 2.62 | 0.258 | 3.4% |
| 5.5 | 0.80 | 0.230 | 14.2% |

It is found that it is impossible to obtain agglomerated zeolitic adsorbents which combine both a maximum adsorption capacity and a maximum mechanical strength. An optimum adsorption capacity/optimum mechanical strength compromise is then obtained for a content of non-zeolitic phase of the order of 3% by weight, with respect to the weight of the agglomerate, measured by XRD according to the method described above.

Example 3

Agglomerates Based on Crystals of NaX of 0.8 µm 200 g of agglomerates obtained from the powder synthesized in Example B are placed in a glass reactor provided with a jacket regulated at a temperature of 100° C.±1° C., 1.5 l of an aqueous sodium hydroxide solution having a concentration of 100 g/l are then added and the reaction medium is left stirring for a period of time which can vary from 1 hour to 8 hours, as shown in the table below.

The agglomerates are subsequently washed in 3 successive operations of washing with water, followed by the emptying of the reactor. It is ascertained that the washing is effective by measuring the final pH of the aqueous wash liquors, which is between 10.0 and 10.5.

These agglomerates are exchanged, as described in Example 1, by means of a 0.5M barium chloride aqueous solution at 95° C. in 4 stages. At each stage, the ratio of volume of solution to weight of solid is 20 ml/g and the exchange is continued for 4 hours on each occasion. Between each exchange, the solid is washed several times so as to free it from the excesses of salt. The agglomerates are subsequently dried at 80° C. for 2 hours and finally activated at 250° C. for 2 hours under a stream of nitrogen.

The various products are characterized in order to determine, by all the analytical techniques described above: the loss on ignition, the content of non-zeolitic phase, the micropore volume and the mechanical strength. The results are given in Table 3 below.

The degree of barium exchange of the agglomerates, calculated from the elemental analyses of the barium oxide and sodium oxide by WDXRF as described in the characterization techniques, is 99.7±0.2%. The loss on ignition, measured as described above, is 5.3%±0.1% for each sample.

TABLE 3

| Duration (h) | BS (MPa) | DR Vol (cm³/g) | NZP (XRD) |
|---|---|---|---|
| 1 | 1.50 | 0.248 | 6.8% |
| 4 | 2.20 | 0.260 | 2.3% |
| 8 | 0.80 | 0.245 | 7.9% |

Example 4

Agglomerates Based on Crystals of NaMSX 200 g of agglomerates obtained from powder formed of NaMSX (K. Schumann et al., *Microporous and Mesoporous Materials*, 154 (2012), 119-123) are placed in a glass reactor provided with a jacket regulated at a temperature of 100±1° C., 1.5 l of an aqueous sodium hydroxide solution having a concentration of 100 g/l are then added and the reaction medium is left stirring for a period of time which can vary from 1 to 8 hours, as shown in Table 4 below.

The agglomerates are subsequently washed in 3 successive operations of washing with water, followed by the emptying of the reactor. It is ascertained that the washing is effective by measuring the final pH of the aqueous wash liquors, which is between 10.0 and 10.5.

These agglomerates are exchanged, as described in Example 1, by means of a 0.5M barium chloride solution at 95° C. in 4 stages. At each stage, the ratio of volume of solution to weight of solid is 20 ml/g and the exchange is continued for 4 hours on each occasion. Between each exchange, the solid is washed several times so as to free it from the excesses of salt. The agglomerates are subsequently dried at 80° C. for 2 h and finally activated at 250° C. for 2 hours under a stream of nitrogen.

The various products are characterized in order to determine, by all the analytical techniques described above: the loss on ignition, the content of non-zeolitic phase, the micropore volume and the mechanical strength. The results are given in Table 4 below.

The degree of barium exchange of the agglomerates, calculated from the elemental analyses of the barium oxide and sodium oxide by WDXRF as described in the characterization techniques, is 99.8±0.2%. The loss on ignition, measured as described above, is 5.4%±0.1% for each sample.

TABLE 4

| Duration (h) | BS (MPa) | DR Vol (cm$^3$/g) | NZP |
|---|---|---|---|
| 1 | 1.90 | 0.242 | 7.3% |
| 4 | 2.90 | 0.254 | 2.7% |
| 8 | 1.20 | 0.238 | 8.8% |

Example 5

Breakthrough Test

A breakthrough (frontal chromatography) test is subsequently carried out on the agglomerated zeolitic adsorbents described in Examples 1 and 3 in order to evaluate their effectiveness. The amount of adsorbent used for these tests is approximately 74 g.

The procedure for obtaining the breakthrough curves is as follows:
Filling the column via the sieve and installing in the test bed.
Filling with the solvent (para-diethylbenzene) at ambient temperature.
Gradual rise to the adsorption temperature under a stream of solvent (5 cm$^3$/min).
Injection of solvent at 10 cm$^3$/min when the adsorption temperature is reached.
Solvent/feedstock interchange in order to inject the feedstock (10 cm$^3$/min).
The injection of the feedstock is subsequently maintained for a time sufficient to reach thermodynamic equilibrium.
Collection and analysis of the effluent from the breakthrough.
The pressure is sufficient for the feedstock to remain in the liquid phase, i.e. 1 MPa. The adsorption temperature is 175° C.

The composition of the feedstock is as follows:
para-Xylene: 45% by weight
meta-Xylene: 45% by weight
Iso-octane: 10% by weight (the latter is used as tracer in order to estimate the nonselective volumes and is not involved in the separation)

The results resulting from the analysis of the breakthrough curves as described in the characterization techniques are recorded in Table 5 below and are compared with the results obtained with the adsorbent according to the prior art (Example 4 of Patent FR 2 903 978) from the breakthrough test carried out under the same conditions as described above.

TABLE 5

| Nature of the solid | DR Vol (cm$^3$/g) | NZP | LOI[1] at 900° C. | Capacity[2] | Selectivity[3] $\alpha_{PX/MX}$ | Height of theoretical plate (cm) |
|---|---|---|---|---|---|---|
| Agglomerate based on crystals of BaX of 1.6 μm (Ex. 4, FR 2 903 978) | 0.256 | 5.5% | 6.0% | 0.194 | 3.33 | 2.26 |
| Agglomerate based on crystals of BaX of 1.0 μm (Ex. 1) | 0.258 | 3.4% | 5.4% | 0.214 | 3.67 | 2.17 |
| Agglomerate based on crystals of BaX of 0.8 μm (Ex. 3) | 0.260 | 2.3% | 5.3% | 0.217 | 3.71 | 1.98 |

[1]LOI: Loss on ignition
[2]The capacity is expressed in cm$^3$ of aromatic C$_8$ hydrocarbons adsorbed per gram of adsorbent as is
[3]PX: para-xylene; MX: meta-xylene It is found that the agglomerated zeolitic adsorbents according to the invention simultaneously combine an improved capacity, an improved selectivity and an improved material transfer in comparison with the adsorbents of the prior art, in particular those described in FR 2 903 978.

The invention claimed is:

1. An agglomerated zeolitic adsorbent, comprising crystals of zeolite X and at least one non-zeolitic phase, wherein:
   the crystals of zeolite X exhibit:
   i. a number-average diameter of less than or equal to 1.5 μm and
   ii. an Si/Al atomic ratio of between 1.2 and 1.50, limits included,
   the content by weight of non-zeolitic phase (NZP) is such that 2.0%<NZP<5.0%, by weight of the total weight of the adsorbent,
   the content by weight of barium oxide (BaO) is greater than 23%, with respect to the total weight of the adsorbent,
   the content by weight of potassium oxide (K$_2$O) is less than 9%, with respect to the total weight of the adsorbent, and
   the total content by weight of oxides of alkali metal or alkaline earth metal ions, other than BaO and K$_2$O, is less than 5% with respect to the total weight of the adsorbent.

2. An adsorbent according to claim 1, wherein the number-average diameter of the crystals of zeolites X is between 0.1 μm and 1.5 μm, limits included.

3. An absorbent according to claim 1, wherein the content of barium oxide (BaO) is between 33% and 42%, limits included, by weight, with respect to the total weight of the adsorbent.

4. An absorbent according to claim 1, the loss on ignition of which, measured at 950° C. according to Standard NF EN 196-2 is between 4.0% and 7.7%, limits included.

5. An absorbent according to claim 1, in the form of agglomerates, the number-average diameter of which is between 0.4 mm and 2 mm, limits included.

6. A process for the preparation of an adsorbent according to claim 1, comprising at least the stages of:
   a) agglomeration of crystals of zeolite X with a number-average diameter of less than or equal to 1.7 μm, with an Si/Al atomic ratio of between 1.2 and 1.50, limits included, with a zeolitisable binder comprising at least 80% by weight of zeolitisable clay and with a source of silica, then shaping of agglomerates and, finally, drying and calcination of said agglomerates,
   b) zeolitization of the said zeolitisable binder by bringing the agglomerates obtained in stage a) into contact with a basic alkaline solution,
   c) cationic exchange of the agglomerates of stage b) by bringing the agglomerates into contact with a solution of barium ions or of barium ions and potassium ions,
   d) optional cationic exchange by bringing the agglomerates of stage c) into contact with a solution of potassium ions,
   e) then washing and drying the agglomerates thus obtained, and
   f) production of the zeolitic adsorbent by activation of the agglomerates obtained in stage e).

7. A process according to claim 6, in which stage b) of zeolitization is carried out with an alkaline solution, the concentration of which is between 0.5M and 5M.

8. A process according to claim 6, in which stage b) of zeolitization is carried out for a period of time of between 1 hour and 8 hours.

9. An adsorbent, obtained according to the process of claim 6.

10. A process for using an adsorbent according to claim 1 wherein the process comprises:
   separating fractions of aromatic $C_8$ isomers,
   separating substituted toluene isomers,
   separating cresols, or
   separating polyhydric alcohols.

11. A process according to claim 10, wherein the process comprises separating para-xylene from fractions of aromatic isomers having 8 carbon atoms.

12. A process for the recovery of para-xylene from fractions of aromatic hydrocarbon isomers comprising 8 carbon atoms, in the liquid phase, by adsorption of the para-xylene using an adsorbent according to claim 1, in the presence of a desorbent.

13. A process according to claim 12, wherein the process is a simulated moving bed process.

14. A process according to claim 12, wherein the process is a simulated countercurrent process.

15. A process according to claim 12, wherein the process is a simulated cocurrent process.

16. A process for the recovery of para-xylene from fractions of aromatic hydrocarbon isomers comprising 8 carbon atoms, in the gas phase, by adsorption of the para-xylene using an adsorbent according to claim 1, in the presence of a desorbent.

17. A process for the recovery of para-xylene according to claim 12, wherein the desorbent is selected from the group consisting of toluene and para-diethylbenzene.

18. A process for the separation of polyhydric alcohols, wherein the process employs an adsorbent according to claim 1.

19. A process for the separation of substituted toluene isomers, wherein the process employs an adsorbent according to claim 1.

20. A process for the separation of cresols, wherein the process employs an adsorbent according to claim 1.

* * * * *